United States Patent [19]

Heimke et al.

[11] 4,287,616
[45] Sep. 8, 1981

[54] AUDITORY OSSICLE PROSTHESIS

[75] Inventors: Gunther Heimke, Weinheim; Dietrich Plester; Klaus Jahnke, both of Tubingen, all of Fed. Rep. of Germany

[73] Assignee: Friedrichsfeld GmbH, Mannheim, Fed. Rep. of Germany

[21] Appl. No.: 118,910

[22] Filed: Feb. 6, 1980

[30] Foreign Application Priority Data

Feb. 10, 1979 [DE] Fed. Rep. of Germany ....... 2905183
Sep. 19, 1979 [DE] Fed. Rep. of Germany ....... 2937842

[51] Int. Cl.³ ............................................... A61F 1/24
[52] U.S. Cl. .......................................................... 3/1.9
[58] Field of Search ........................................ 3/1, 1.9

[56] References Cited

U.S. PATENT DOCUMENTS 3,473,170 10/1969 Haase et al. .................. 3/1
4,130,905 12/1978 Mercandino ............................. 3/1.9

FOREIGN PATENT DOCUMENTS 1926587 5/1969 Fed. Rep. of Germany ........... 3/1.9
1083769 9/1967 United Kingdom .................... 3/1.9
1191022 5/1970 United Kingdom ................... 3/1.9

OTHER PUBLICATIONS

"Teflon Umbrella Columnella", As Design by David Austin, M.D., Micro-Surgery Instruments & Implants (Catalog), Richards Mfg. Co., 1450 Brooks Rd., Memphis, Tenn., p. 29, Copyright 1965.
"Experimental Analysis of Ceramic-Tissue Interactions, A Morphologic, Fluoroescenseoptic, and Radiographic Study of Dense Alumina-oxide Ceramic in Various Animals", by Peter Griss et al., Journal Biomedical Materials Research Symposium, No. 5, (Part 1), pp. 39–48, 1974.

*Primary Examiner*—Ronald L. Frinks
*Attorney, Agent, or Firm*—Fisher, Christen & Sabol

[57] ABSTRACT

An auditory ossicle prosthesis comprises a grooved plate and a depending shaft integrally formed as a one-piece construction from a biologically inert ceramic material, provided with a hole extending through the plate and along the interior of the shaft to reduce the amount of material to be removed by grinding when the device is fitted to the patient.

5 Claims, 5 Drawing Figures

AUDITORY OSSICLE PROSTHESIS

BACKGROUND OF THE INVENTION

The present invention concerns a one-piece auditory ossicle prosthesis consisting of a plate and of a shaft attached to it.

Such prostheses are necessary for reconstructing the complete auditory ossicular chain and thus to improve hearing if the complete auditory ossicular chain is fully or partially destroyed by chronic inflammations of the middle ear or by other injuries. Since there are, in general, no two identical cases in which a curative and hearing-improving operation on the middle ear (tympanoplasty) is necessary, it is necessary to have the possibility to adjust the needed implant to the actual individual conditions.

The implants used hitherto consist of different plastics, e.g., silicones. Implants made of porous plastics are also in use already. They always consist of a round plate and a shaft attached centrally to one side of the plate, with the axis of the said shaft being perpendicular to the plane of the plate.

These implants have the disadvantage that they cannot be processed adequately intraoperatively, because such soft plastics spring back strongly during grinding or cutting. Moreover, such plastics have only a limited compatibility with the body, i.e., some foreign-body-induced giant cells are found usually on their interface with the bony tissue and extrusion of the plastic implant may occur.

SUMMARY OF THE INVENTION

The present invention therefore has the basic task of finding implants which either require no working at all intraoperatively, or if they are to be worked intraoperatively, lend themselves to such working at high precision and reliably maintain the shape created by the working. Another task of the present invention is to provide such implants made from a really biologically-inert material.

The task is solved according to the present invention in such a way that the plate 1 has at least one groove 4 on the side 3 opposed to the side carrying the shaft 2.

According to another embodiment of the present invention, the plate 1 has a set of grooves 5, 6, 7 on the side 3 that is opposed to the side carrying the shaft. Adjustment to the plane of the tympanic membrane is possible by means of an auditory ossicle prosthesis in which the axis 8 of the shaft is inclined relative to the normal 9 of the plate at an angle of about 30° and in which the groove or the grooves 10, 11 run parallel to the plane which is determined by the normal 9 of the plate and the axis 8 of the shaft. It is advantageous if the auditory ossicle prostheses of the above-described type consist of a biologically-inert material. Alumina ceramic with an $Al_2O_3$ content of more than 99 wt.% has proved to be suitable as a biologically-inert material in the sense of the word as understood above for the auditory ossicle prostheses. p An auditory ossicle prosthesis according to the present invention offers the advantage that it can be brought by the surgeon exactly to the fitting shape intraoperatively. This additional processing can, however, be limited to the correction of the shaft length, since the grooves 4, 5, 6, 7, 10 and 11 are already present. By the use of biologically-inert material for the auditory ossicle prosthesis, the rejection reactions, which are manifested usually through the formation of foreign-body-induced giant cells at the boundary of the implant can be avoided. The expression "biologically-inert" is applied here to materials which induce no defense reactions of the body following implantation, which reactions would be manifested in the formation of foreign body-induced giant cells at the boundary with the implant. The materials which satisfy these conditions are high-purity alumina ceramic with more than 99 wt.% $Al_2O_3$ and also some carbon modifications.

According to another embodiment of the invention, in addition to the the aforementioned grooves, the plate 1 and the shaft 2 may be provided with a hole going through both elements.

This hole can be arranged especially advantageously coaxially to the shaft. It is especially simple, especially technologically, if the hole has a constant cross-section all over its length.

An auditory ossicle prosthesis, which possesses these additional characteristics, has the following advantages:

The weight of the entire prosthesis is reduced. The prosthesis is maintained in its position by a relatively weak tension that can be generated between the remaining parts of the complete auditory ossicle. Since most of the biologically-inert materials that can be considered for this prosthesis have a specific gravity that is higher than that of the natural bone, the forces generated thereby could lead to undesirable bone reactions. The accelerative forces inherently resulting from the higher density of the prosthesis could also have adverse effects in case of accident. Such hazards are diminished by the weight reduction brought about by the hole piercing the plate and the shaft.

The shaft length of such auditory ossicle prosthesis is adjusted to the individual anatomic conditions intraoperatively, e.g., by grinding. The processing is facilitated substantially if less material needs to be removed when shortening the shaft. The hole going through the shaft reduces the amount of the material to be ground off intraoperatively. If the length is correct, the shaft can be placed directly onto the caput stapedis (3rd auditory ossicle).

In some indications, the implantation of a tympanic tubule is advantageous or necessary. In such cases, it is possible to transform an auditory ossicle prosthesis according to the present invention into a tympanic tubule by corresponding additional working.

DESCRIPTION OF THE PREFERRED EMBODIMENTS

Figure 1:
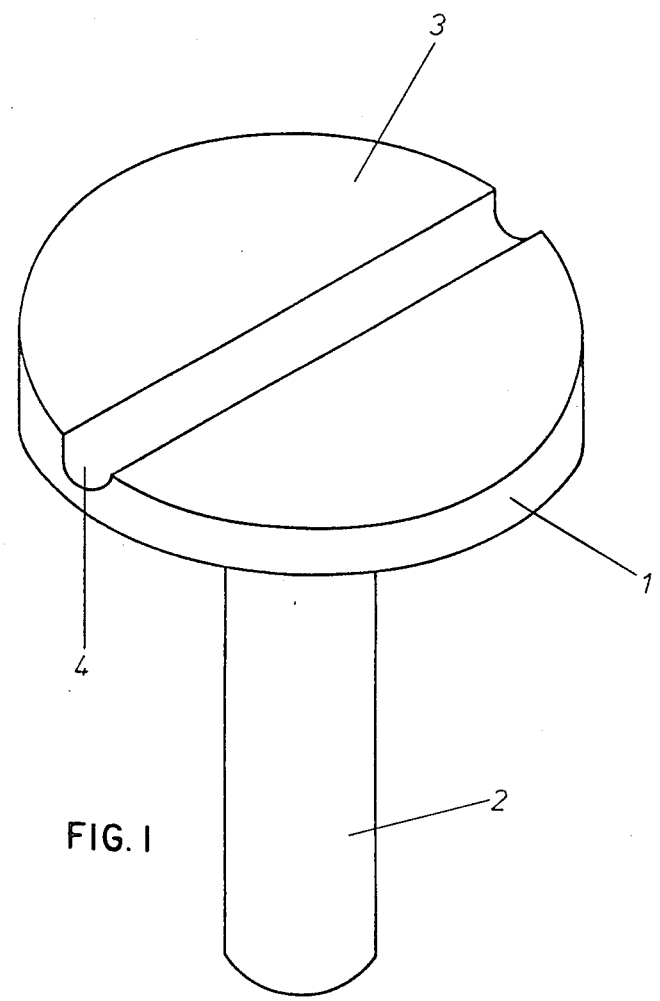
FIG. 1 shows a preferred embodiment of an auditory ossicle prosthesis in accordance with the invention having a single groove.
Figure 2:
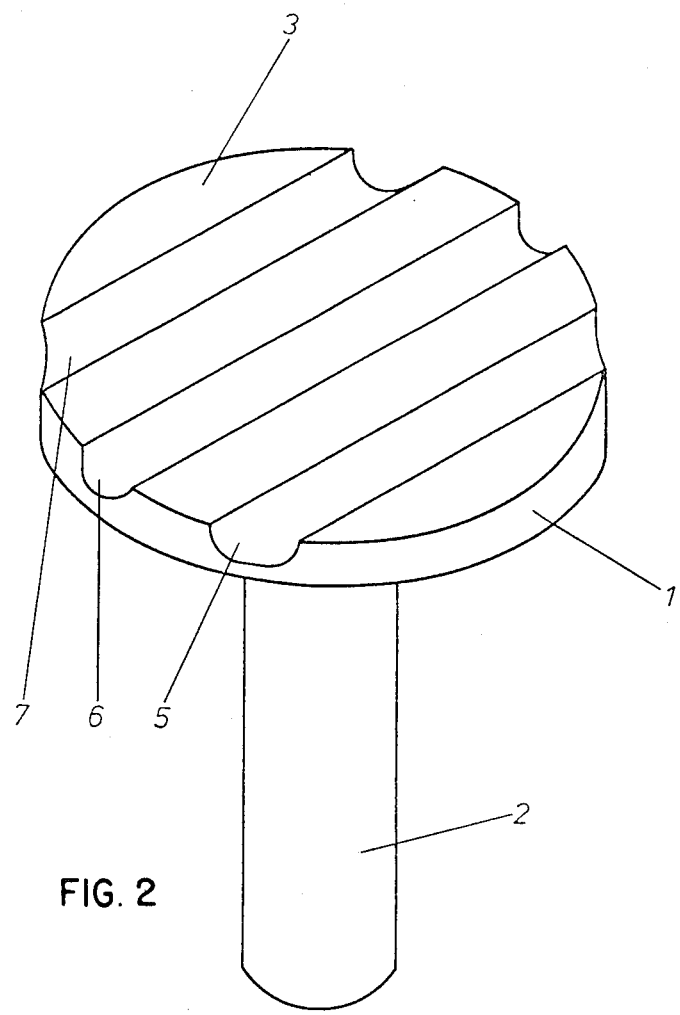
FIG. 2 illustrates an auditory ossicle prosthesis with three parallel grooves.
Figure 3:
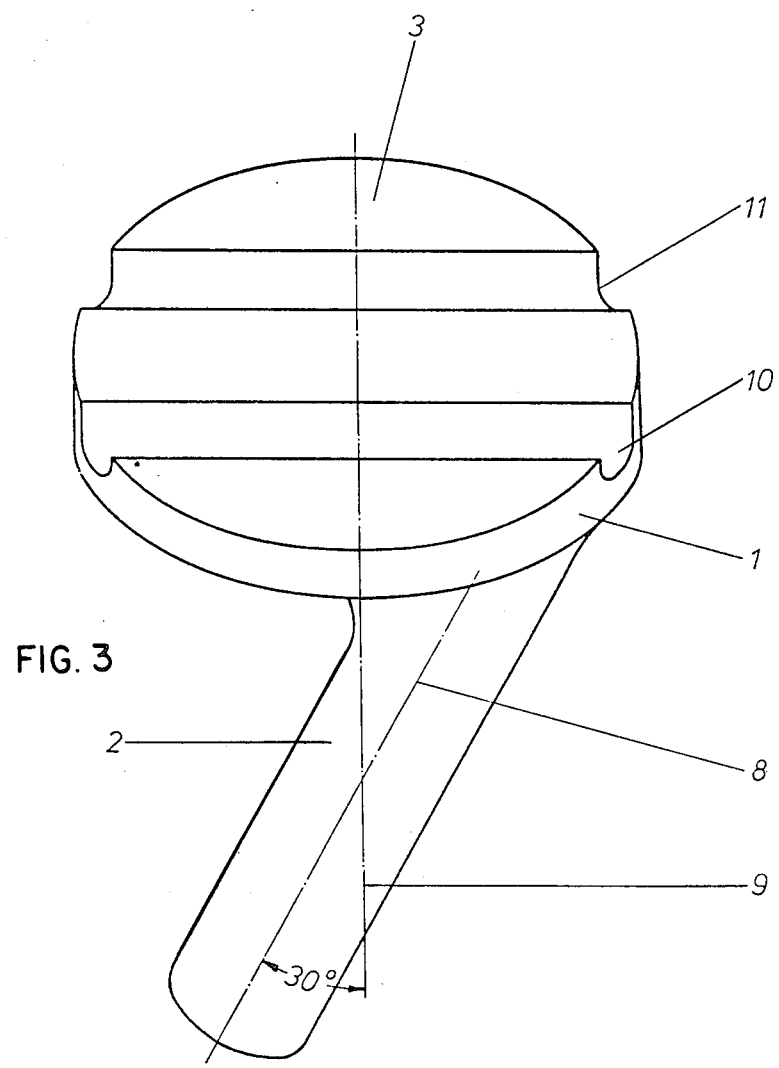
FIG. 3 shows an auditory ossicle prosthesis provided with an inclined shaft.

In the Figures, the plate is designated by 1 and the shaft of the prosthesis by 2. The side of the plate 1 that is opposed to the shaft, which side carries the groove 4 according to the present invention in FIG. 1, is designated by 3. FIG. 2 shows a prosthesis in which the plate 1 carries three parallel grooves 5, 6, and 7 on the side 3 opposed to the shaft 2. FIG. 3 shows a prosthesis in which the shaft 2 is inclined relative to the plate 1. Here, the axis of the shaft 2 is designated by 8 and the normal of the plate 1 by 9. In the top side 3 of the plate 1, there are two grooves 10 and 11, which are parallel to the plane formed by the axis 8 of the shaft and the normal 9 of the plate.

During the implantation of such a prosthesis, due to the presence of the groove 4 and of the grooves 5, 6, 7, 10, or 11, it is possible to firmly position the manubrium mallei as a remaining rest of the auditory ossicle, into the groove, namely, approximately in the center of the implant. Therefore only the shaft 2 needs be ground off to the actually-needed length. The biologically-inert materials intended for use permit a high-precision working. The necessary tools, such as diamond-tipped cutters, belong to the standard surgical instrumentarium of this discipline.

Figure 4A:
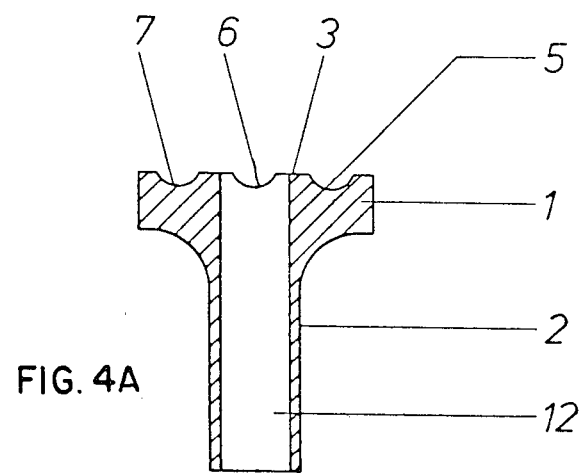
FIGS. 4A and 4B illustrates a modified form of the invention provided with a hole extending through the plate and shaft.
Figure 4B:
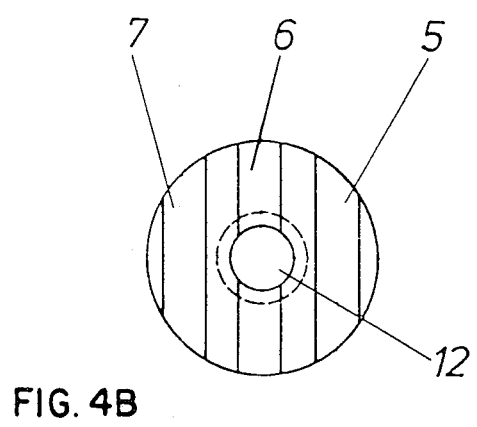

In FIGS. 4A and 4B, the plate is designated by 1 and the shaft of the auditory ossicle prosthesis by 2. On that side 3 of the plate that is opposed to the shaft, the prosthesis carries the grooves designated by 5, 6, and 7. The hole going through the plate 1 and the shaft 2 according to the present invention is designated by 12. In this case, this hole goes through the plate and the shaft coaxially and has a constant cross-section.

The shaft length is adjusted to the individual anatomic conditions as in the other modifications, e.g. by grinding, the adjustment being facilitated by the fact that less material needs to be removed because the hole through the shaft reduces the amount of the material present.

We claim:

1. Auditory ossicle prosthesis comprising a rigid plate and a depending tubular shaft formed integrally as a one-piece construction from a biologically inert ceramic material, the surface of the plate on the side away from the shaft being provided with a plurality of grooves.

2. Prosthesis according to claim 1, wherein the axis of the shaft is inclined at an angle of approximately 30° with respect to the grooved surface of the plate, and the grooves are parallel with a plane passing through the axis of the shaft and normal to the plane of the gooved surface.

3. Prosthesis according to either one of claims 1 or 2, wherein the cross-section of said shaft is uniform along its entire length.

4. Prosthesis according to either one of claims 1 or 2, wherein said ceramic material comprises alumina ceramic having an $Al_2O_3$ content of at least 99.0 percent by weight.

5. Prosthesis according to claim 3, wherein said ceramic material comprises alumina ceramic having an $Al_2O_3$ content of at least 99.0 percent by weight.

* * * * *